(12) United States Patent
Qin et al.

(10) Patent No.: US 11,458,188 B2
(45) Date of Patent: Oct. 4, 2022

(54) ABC TRANSPORTER PEPTIDE INHIBITOR XH-14C AND APPLICATION THEREOF

(71) Applicant: HUNAN UNIVERSITY OF SCIENCE AND ENGINEERING, Hunan (CN)

(72) Inventors: Zuodong Qin, Hunan (CN); Xiaofang Luo, Hunan (CN); Luya Feng, Hunan (CN); Zongcheng Wang, Hunan (CN)

(73) Assignee: HUNAN UNIVERSITY OF SCIENCE AND ENGINEERING, Yongzhou (CN)

( * ) Notice: Subject to any disclaimer, the term of this patent is extended or adjusted under 35 U.S.C. 154(b) by 0 days.

(21) Appl. No.: 17/324,063

(22) Filed: May 18, 2021

(65) Prior Publication Data
US 2021/0315965 A1  Oct. 14, 2021

(30) Foreign Application Priority Data
May 18, 2020  (CN) .......................... 202010416646.3

(51) Int. Cl.
*A61K 38/10* (2006.01)
*A61K 45/06* (2006.01)

(52) U.S. Cl.
CPC .............. *A61K 38/10* (2013.01); *A61K 45/06* (2013.01)

(58) Field of Classification Search
CPC .................................. A61K 38/10; C70K 7/08
See application file for complete search history.

(56) References Cited

U.S. PATENT DOCUMENTS
2009/0208493 A1  8/2009  Larson et al.

FOREIGN PATENT DOCUMENTS
CN  102274220 A  12/2011
CN  110478487 A  11/2019

OTHER PUBLICATIONS

Teng et al., "The Multidrug Resistance-Reversing Activity of a Novel Antimicrobial Peptide", Cancers, Jul. 19, 2020 (Year: 2020).*

* cited by examiner

*Primary Examiner* — Lianko G Garyu

(57) ABSTRACT

Provided are an ABC transporter peptide inhibitor XH-14C and an application thereof in the treatment of a tumor with multidrug resistance mediated by an ABC transporter. In the application, the peptide inhibitor XH-14C shown in SEQ ID NO: 1 is administered in combination with an ABC transporter substrate chemotherapeutic drug. This disclosure also provides a pharmaceutical composition for treating a tumor with multidrug resistance mediated by the ABC transporter, containing the peptide XH-14C shown in SEQ ID NO: 1 and an ABC transporter substrate chemotherapeutic drug.

9 Claims, 9 Drawing Sheets

Specification includes a Sequence Listing.

```
                        SEQUENCE LISTING

<160> NUMBER OF SEQ ID NOS: 3

<210> SEQ ID NO 1
<211> LENGTH: 14
<212> TYPE: PRT
<213> ORGANISM: Artificial Sequence
<220> FEATURE:
<223> OTHER INFORMATION: synthetic

<400> SEQUENCE: 1

Phe Ile Lys Arg Ile Ala Arg Leu Leu Arg Lys Ile Trp Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetic

<400> SEQUENCE: 2

Phe Phe Arg Lys Val Leu Lys Leu Ile Arg Lys Ile
1               5                   10

<210> SEQ ID NO 3
<211> LENGTH: 13
<212> TYPE: PRT
<213> ORGANISM: Artificial Sequence
<220> FEATURE:
<223> OTHER INFORMATION: synthetic

<400> SEQUENCE: 3

Phe Phe Arg Lys Val Leu Lys Leu Ile Arg Lys Ile Phe
1               5                   10
```

ABC TRANSPORTER PEPTIDE INHIBITOR XH-14C AND APPLICATION THEREOF

REFERENCE TO AN ELECTRONIC SEQUENCE LISTING

The contents of the electronic sequence listing (Sequence Listing-20210629.txt; Size: 1,000 bytes; and Date of Creation: Jun. 29, 2021) is herein incorporated by reference in its entirety.

CROSS-REFERENCE TO RELATED APPLICATIONS

This application claims the benefit of priority from Chinese Patent Application No. 202010416646.3, filed on May 18, 2020. The content of the aforementioned application, including any intervening amendments thereto, is incorporated herein by reference in its entirety.

TECHNICAL FIELD

This application relates to tumor treatment, and more particularly to an ABC transporter peptide inhibitor XH-14C and an application thereof.

BACKGROUND

In the tumor treatment, the occurrence of multidrug resistance is the most important factor causing the chemotherapy failure and tumor recurrence. The molecular mechanism of the tumor multidrug resistance is relatively complex, while it has been found that the high expression of the ATP-binding cassette transporter superfamily (ABC family) in tumor tissues is the main cause for the tumor multidrug resistance. As a main member in the ABC transporter family, ABCB1 and ABCC1 are highly expressed in a variety of tumor tissues, for example, ABCB1 is highly expressed in human oral epidermal cancer cells, colon cancer cells, liver cancer cells and prostate cancer cells; ABCC1 exhibits high expression in lung cancer cells, liver cancer cells, intestinal cancer cells and breast cancer cells. ABCB1 and ABCC1 can identify a variety of antitumor chemotherapeutics, and then pump chemotherapeutic drugs out of tumor cells using the energy released by ATP hydrolysis, so that the concentration of chemotherapeutic drugs in the tumor cells is reduced, and the efficacy of chemotherapeutic drugs is weakened or even disappears. Therefore, the combination of an ABC transporter inhibitor and traditional chemotherapeutic drugs to reduce or inhibit the expression of ABC transporter and increase the concentration of chemotherapeutic drugs in the drug-resistant tumor cells is considered as a clinically effective strategy to overcome ABC transporter-mediated multidrug resistance. However, the existing ABC transporter inhibitors are greatly limited in the clinical application due to poor selectivity, interaction with chemotherapeutic drug, and low safety. Therefore, it is of great significance to develop a novel ABC transporter inhibitor with high efficiency, low toxicity and strong selectivity to overcome the drug resistance of tumors.

Peptides are widely found in animal and plant tissues. Many peptides have special functions in organisms, and are collectively referred to as bioactive peptides. Recently, the bioactive peptides have been demonstrated to play an important role in many fields of life sciences, such as immune defense, reproduction control, tumorigenesis and anti-aging. Among the bioactive peptides, antimicrobial peptides (AMP) and antitumor peptides (APC) have been studied extensively. AMP refers to a class of peptide molecules secreted by a variety of organisms such as invertebrates, plants and animals, which can effectively kill foreign pathogens such as bacteria, fungi, viruses, etc., and are a part of the natural immune system of organisms. APC refers to a class of peptides that inhibit the growth and proliferation of tumor cells, and most of them are derived from AMP. Most AMP and APC have similar structural characteristics, that is, they are generally composed of 10-40 amino acids, and have positively charged polar amino acids and a certain proportion of non-polar amino acids, thus showing amphiphilicity. AMP and APC act very quickly, such that the tumor cells are not easy to develop drug resistance. In view of this, the peptides have become a research hotspot in the development of new drugs.

After the asymmetric distribution of phospholipids in tumor cell membranes is destroyed, phosphatidylethanolamine (PE) and phosphatidylserine (PS) appear in large quantities on the outer layer of the cell membrane. At this time, through the electrostatic attraction between the positively charged polar amino acids in the peptide chain and the negatively charged phospholipids (PS) on the surface of the tumor cell membrane, the peptide is aggregated on the surface of the tumor cell membrane.

The aggregated peptide presents an α-helical structure, in which the hydrophobic amino acids on the non-polar side can extend into the inner layer of the cell membrane by hydrophobic interaction, thereby further exerting an antitumor effect by the mechanism of membrane lysis and non-membrane lysis. In the previous researches related to the drug resistance of tumors, peptides are generally used as anti-cancer agents. Although they have certain selectivity for tumor cells, they are also toxic to normal cells at an effective tumor-inhibiting concentration, which limit their clinical application.

SUMMARY

An object of this application is to provide an application of a combination of an ABC transporter inhibitor and an ABC transporter substrate chemotherapeutic drug in the preparation of a drug for treating an ABC transporter-mediated multidrug resistance tumor.

The technical solutions of this application are described as follows.

In a first aspect, this application provides an ABC transporter peptide inhibitor, wherein the ABC transporter peptide inhibitor is peptide XH-14C shown in SEQ ID NO: 1.

In a second aspect, this application provides a method of treating a tumor with multidrug resistance mediated by an ABC transporter in a subject in need thereof, comprising:
administering the peptide XH-14C shown in SEQ ID NO: 1 to the subject.

In a third aspect, this application provides a method of treating a tumor with multidrug resistance mediated by an ABC transporter in a subject in need thereof, comprising:
administering a composition of the peptide XH-14C shown in SEQ ID NO: 1 and an ABC transporter substrate chemotherapeutic drug to the subject;
wherein the ABC transporter is ABCB1 or ABCC1.

In some embodiments, when the ABC transporter is ABCB1, the ABC transporter substrate chemotherapeutic drug is selected from the group consisting of taxanes, vinca alkaloids, anthracyclines, epipodophyllotoxins, tyrosine kinase inhibitors and antitumor antibiotics; and when the ABC transporter is ABCC1, the ABC transporter substrate chemotherapeutic drug is selected from the group consisting of vinca alkaloids, anthracyclines, epipodophyllotoxins and tyrosine kinase inhibitors.

In some embodiments, when the ABC transporter is ABCB1, the ABC transporter substrate chemotherapeutic drug is selected from the group consisting of paclitaxel, docetaxel, vinblastine, vincristine, doxorubicin, daunorubicin, etoposide, teniposide, imatinib, nilotinib, erlotinib, actinomycin D and a combination thereof; and when the transporter is ABCC1, the ABC transporter substrate chemotherapeutic drug is selected from the group consisting of anthracycline, vinca alkaloid, epipodophyllotoxin, camptothecin, methotrexate, saquinavir, mitoxantrone, imatinib and a combination thereof.

In some embodiments, when the ABC transporter is ABCB1, the tumor is lung cancer, cervical cancer, human epidermoid carcinoma, ovarian cancer, liver cancer, intestinal cancer, gastric cancer or pancreatic cancer; and when the ABC transporter is ABCC1, the tumor is lung cancer, liver cancer, intestinal cancer, breast cancer or esophageal cancer.

In a fourth aspect, this application provides a pharmaceutical composition for treating a tumor with multidrug resistance mediated by an ABC transporter, comprising:
the peptide XH-14C shown in SEQ ID NO: 1 and an ABC transporter substrate chemotherapeutic drug.

In some embodiments, the ABC transporter is ABCB1 or ABCC1.

In some embodiments, when the ABC transporter is ABCB1, the ABC transporter substrate chemotherapeutic drug is selected from the group consisting of taxanes, vinca alkaloids, anthracyclines, epipodophyllotoxins, tyrosine kinase inhibitors and antitumor antibiotics; and when the ABC transporter is ABCC1, the ABC transporter substrate chemotherapeutic drug is selected from the group consisting of vinca alkaloids, anthracyclines, epipodophyllotoxins and tyrosine kinase inhibitors.

In some embodiments, when the ABC transporter is ABCB1, the ABC transporter substrate chemotherapeutic drug is selected from the group consisting of paclitaxel, docetaxel, vinblastine, vincristine, doxorubicin, daunorubicin, etoposide, teniposide, imatinib, nilotinib, erlotinib, actinomycin D and a combination thereof; and when the transporter is ABCC1, the ABC transporter substrate chemotherapeutic drug is selected from the group consisting of anthracycline, vinca alkaloid, epipodophyllotoxin, camptothecin, methotrexate, saquinavir, mitoxantrone, imatinib and a combination thereof.

This application has the following beneficial effects.

This application discloses that the peptide HX-14C can inhibit the function of the ABC transporter, and thus can increase the concentration of the chemotherapeutic drug in the drug-resistant tumor cells when administered in combination with the ABC transporter substrate chemotherapeutic drug, thereby inhibiting the proliferation of the drug-resistant tumor cells. The combination of the ABC transporter peptide inhibitor provided herein and the ABC transporter substrate chemotherapeutic drug has a promising application prospect in the treatment of tumors with multidrug resistance mediated by the ABC transporter.

The peptide provided herein plays a role in reversing the multidrug resistance of tumors mediated by the ABC transporter at a non-cytotoxic concentration by inhibiting the function of the ABC transporter, showing better safety and brilliant application prospect.

DETAILED DESCRIPTION OF EMBODIMENTS

Figure 1A:
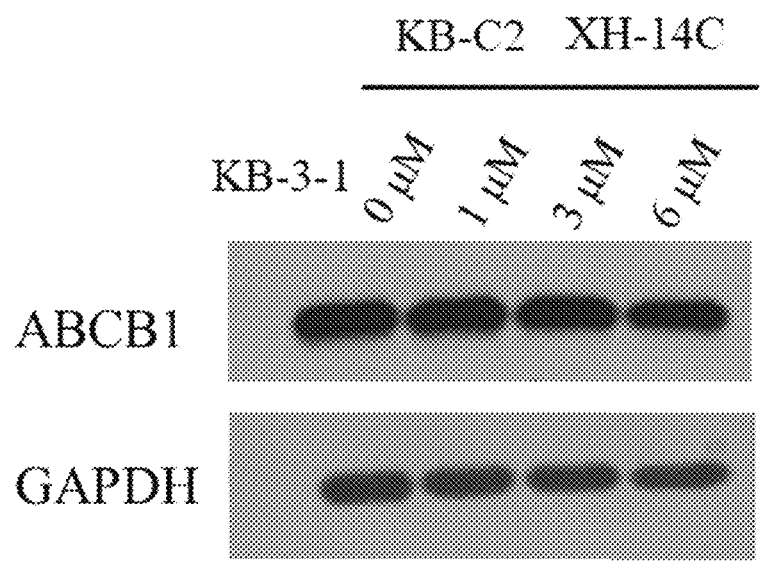
FIG. 1A shows expression of ABCB1 protein in KB-C2 cells after incubation with different concentrations of peptide XH-14C for 72 h, where KB-3-1 cells without any treatment are used as negative control, and glyceraldehyde-3-phosphate dehydrogenase (GAPDH) is used as loading control.

The disclosure will be further illustrated with reference to the accompanying drawings and embodiments. The experiments in the embodiments are all performed using conventional procedures unless otherwise specified. Materials, reagents and the like used in the following embodiments are commercially available unless otherwise specified. It should be understood that these embodiments are merely illustrative of the present disclosure, and are not intended to limit the scope of the present disclosure.

The peptides described below are synthesized by solid phase synthesis. Optionally, the synthesis can also be entrusted to a commercial company.

EXAMPLE 1

Effect of Peptide XH-14C on ABCB1-Overexpressing Cell Lines

To investigate the effect of the peptide XH-14C on the ABC transporter, the sensitivity of ABCB1-overexpressing cells KB-C2 to the peptide XH-14C was determined. The cytotoxicity of the peptide in different cell lines was measured by modified MTT assay. 5,000 cells per well were seeded in a 96-well microplate and cultured overnight.

Peptides and positive control were added in a designated concentration gradient. The plate was incubated for 68 h, and then added with 20 μL of MTT solution (4 mg/mL) per well and incubated for another 4 h. The medium was pipetted, to which 100 μL of DMSO was added to dissolve the formaldehyde crystals. The absorbance was measured at 570 nm with a UV/Vis microplate spectrophotometer. The results of the MTT assay were shown in Table 1, from which it can be observed that the IC50 values of the peptides XH-14A (FFRKVLKLIRKI, as shown in SEQ ID NO: 2), XH-14B (FFRKVLKLIRKIF, as shown in SEQ ID NO: 3) and XH-14C (FIKRIARLLRKIWR, as shown in SEQ ID NO: 1) on ABCB1-overexpressing cancer cells (KB-C2) were 22.45 μM, 8.38 μM and 7.35 μM, respectively. The $IC_{50}$ values of the peptides on the parental cells (KB-3-1) were 8.73 μM, 10.02 μM and 8.38 μM, respectively. Significantly, the MTT assay results demonstrated that these three peptides did not produce significant cytotoxicity against cancer cells at a concentration of 3 μM, and were therefore selected for the reversal study.

TABLE 1

Cytotoxicity of peptides

| Treatment | $IC_{50}$ (μM) | |
|---|---|---|
| | KB-3-1 | KB-C2 |
| XH-14A | 8.73 | 22.45 |
| XH-14B | 10.02 | 8.38 |
| XH-14C | 8.37 | 7.53 |
| Paclitaxel | 0.03 | 1.77 |
| Cisplatin | 2.29 | 2.96 |

EXAMPLE 2

Effect of Peptide XH-14C on ABCC1-Overexpressing Cell Lines

To investigate the effect of the peptide XH-14C on the ABC transporter, the sensitivity of ABCC1-overexpressing cells KB-CV60 to the peptide XH-14C was determined. The cytotoxicity of the peptide in different cell lines was measured by modified MTT assay. 5000 cells per well were seeded in a 96-well cell microplate and cultured overnight. Peptide and positive control were added in a designated concentration gradient. The plate was incubated for 68 h, and then added with 20 μL of MTT solution (4 mg/mL) per well and incubated for another 4 h. The medium was pipetted, to which 100 μL of DMSO was added to dissolve the formaldehyde crystals. The absorbance was measured at 570 nm with a UV/Vis microplate spectrophotometer. The results of the MTT assay were shown in Table 2, from which it can be observed that the $IC_{50}$ values of the peptides XH-14A (FFRKVLKLIRKI, as shown in SEQ ID NO:2), XH-14B (FFRKVLKLIRKIF, as shown in SEQ ID NO:3) and XH-14C (FIKRIARLLRKIWR) on ABCC1-overexpressing cancer cells (KB-CV60) were 14.71 μM, 8.54 μM and 10.12 μM, respectively. The $IC_{50}$ values of the peptides on the parental cells (KB-3-1) were 7.18 μM, 7.82 μM, and 8.37 μM, respectively. Significantly, the MTT assay results demonstrated that these three peptides did not produce significant cytotoxicity against cancer cells at a concentration of 3 μM, and were therefore selected for the reversal study.

TABLE 2

Cytotoxicity of peptides

| Treatment | $IC_{50}$ (μM) | |
|---|---|---|
| | KB-3-1 | KB-CV60 |
| XH-14A | 7.18 | 14.71 |
| XH-14B | 7.82 | 8.54 |
| XH-14C | 8.37 | 10.12 |
| Vincristine | 0.095 | 16.06 |
| Cisplatin | 2.29 | 2.96 |

EXAMPLE 3

Investigation on Reversal Effect of Peptide XH-14C on Drug Resistance of ABCB1-Overexpressing Cell Line To determine whether the peptide XH-14C can reverse the ABCB1-mediated multidrug resistance (MDR), the cytotoxicity of the peptide on drug-induced drug-resistant cancer cell lines (KB-C2), transfected ABCB1-overexpressing cell lines (HEK293/ABCB1) (Shi Z, Tiwari A K, Shukla S, et al. Sildenafil Reverses ABCB1—and ABCG2—Mediated Chemotherapeutic Drug Resistance[J]. *Cancer Research*, 2011, 71(8):3029-3041.) and their corresponding parental cell lines (KB -3-1 and HEK293/pcDNA3.1) was tested, and the results were shown in Tables 3 and 4. Compared with the KB-3-1 and HEK293/pcDNA3.1 cell lines, the peptide XH-14C significantly reduced the $IC_{50}$ values of paclitaxel and adriamycin against the ABCB1-overexpressing KB-C2 and HEK293/ABCB1 cell lines. In addition, compared with the corresponding parental cells (KB-3-1 and HEK293/pc DNA3.1), the peptide XH-14C did not affect the $IC_{50}$ values of cisplatin (a non-substrate of ABCB1) on the ABCB1-overexpressing KB-C2 and HEK293/ABCB1 cell lines (Table 4). These results indicated that the peptide XH-14C can reverse the MDR of cancer cells mediated by ABCB1. Under the same conditions, different from the peptide XH-14C, the peptides XH-14A and XH-14B has no reversal effect although they only differed from the peptide XH-14C by 1-2 amino acids.

TABLE 3

Reversal effects of peptides on drug-induced ABCB1-overexpressing cancer cell lines

| Treatment | $IC_{50}$ (μM) ($RF^1$) | |
|---|---|---|
| | KB-3-1 | KB-C2 |
| Paclitaxel | 0.002 (1.00) | 1.430 (715.00) |
| +XH-14A (3 μM) | 0.004 (2.00) | 1.767 (883.50) |
| +XH-14B (3 μM) | 0.003 (1.50) | 0.441 (220.50) |
| +XH-14C (3 μM) | 0.003 (1.50) | 0.038** (19.0) |
| +Verapamil (3 μM) | 0.001 (0.50) | 0.030*** (15.00) |
| Adriamycin | 1.186 (1.00) | 69.79 (58.84) |
| +XH-14A (3 μM) | 1.187 (1.00) | 61.03 (51.46) |
| +XH-14B (3 μM) | 1.010 (0.85) | 15.01 (12.66) |
| +XH-14C (3 μM) | 1.012 (0.85) | 1.454*** (1.23) |
| +Verapamil (3 μM) | 0.897 (0.76) | 0.734*** (0.62) |
| Cisplatin | 1.793 (1.00) | 2.025 (1.13) |
| +XH-14A (3 μM) | 1.626 (0.90) | 1.910 (1.07) |
| +XH-14B (3 μM) | 1.672 (0.93) | 2.150 (1.20) |

TABLE 3-continued

Reversal effects of peptides on drug-induced ABCB1-overexpressing cancer cell lines

| Treatment | IC$_{50}$ (μM) (RF[1]) | |
|---|---|---|
| | KB-3-1 | KB-C2 |
| +XH-14C (3 μM) | 1.693 (0.94) | 2.087 (1.16) |
| +Verapamil (3 μM) | 1.676 (0.93) | 2.107 (1.18) |

[1]RF, resistant fold, calculated by dividing the IC$_{50}$ value in the drug-induced ABCB1-overexpressing cancer cell line KB-C2 by the IC$_{50}$ value in the parental cancer cell line KB-3-1.
\*\*\*means p < 0.001, compared with the value of KB-C2 control group.

TABLE 4

Reversal effects of peptides on transfected ABCB1-overexpressing cancer cell lines

| Treatment | IC$_{50}$ (μM) (RF[1]) | |
|---|---|---|
| | HEK293/pcDNA3.1 | HEK293/ABCB1 |
| Paclitaxel | 1.449 (1.00) | 30.924 (21.34) |
| +XH-14A (3 μM) | 1.508 (1.04) | 24.044 (16.59) |
| +XH-14B (3 μM) | 1.511 (1.04) | 20.917 (14.44) |
| +XH-14C (3 μM) | 1.575 (1.090) | 1.717\*\*\* (1.18) |
| +Verapamil (3 μM) | 1.486 (1.03) | 1.708\*\*\* (1.18) |
| Adriamycin | 1.235 (1.00) | 31.233 (25.29) |
| +XH-14A (3 μM) | 1.254 (1.02) | 23.05 (18.66) |
| +XH-14B (3 μM) | 1.176 (0.95) | 19.42 (15.72) |
| +XH-14C (3 μM) | 1.220 (0.98) | 1.282\*\*\* (1.03) |
| +Verapamil (3 μM) | 1.271 (1.03) | 1.245\*\*\* (1.00) |
| Cisplatin | 2.214 (1.00) | 2.665 (1.20) |
| +XH-14A (3 μM) | 2.272 (1.03) | 2.358 (1.07) |
| +XH-14B (3 μM) | 2.272 (1.03) | 2.358 (1.07) |
| +XH-14C (3 μM) | 2.316 (1.05) | 2.246 (1.01) |
| +Verapamil (3 μM) | 2.128 (0.96) | 2.287 (1.03) |

[1]RF, resistance fold, calculated by dividing the IC$_{50}$ value in the transfected ABCB1-overexpressing cell line HEK293/ABCB1 by the IC$_{50}$ value in the transfected empty vector cell line HEK293/pcDNA3.1.
\*\*\*means p < 0.001, compared with the value of HEK293/ABCB1 control group.

EXAMPLE 4

Investigation on Reversal Effect of Peptide XH-14C on Drug Resistance of ABCC1-Overexpressing Cell Line To determine whether the peptide XH-14C can reverse the ABCC1-mediated multidrug resistance (MDR), the cytotoxicity of the peptide on drug-induced drug-resistant cancer cell lines (KB-CV60), transfected ABCC1-overexpressing cell lines (HEK293/ABCC1) (Shi Z, Tiwari A K, Shukla S, et al. Sildenafil Reverses ABCB1—and ABCG2—Mediated Chemotherapeutic Drug Resistance[J]. *Cancer Research*, 2011, 71(8):3029-3041.) and their corresponding parental cell lines (KB -3-1 and HEK293/pcDNA3.1) was tested, and the results were shown in Tables 5 and 6. Compared with the KB-3-1 and HEK293/pcDNA3.1 cell lines, the peptide XH-14C significantly reduced the IC50 values of vincristine against the ABCC1-overexpressing KB-CV60 and HEK293/ABCC1 cell lines. In addition, compared with the corresponding parental cells (KB-3-1 and HEK293/pc DNA3.1), the peptide XH-14C did not affect the IC50 values of cisplatin (a non-substrate of ABCC1) on the ABCC1-overexpressing KB-CV60 and HEK293/ABCC1 cell lines (Table 4). These results indicated that the peptide XH-14C can reverse the MDR of cancer cells mediated by ABCC1.

TABLE 5

Reversal effects of peptides on drug-induced ABCC1-overexpressing cancer cell lines

| Treamtment | IC$_{50}$ (μM) (RF[1]) | |
|---|---|---|
| | KB-3-1 | KB-CV60 |
| Vincristine | 0.095 (1.00) | 16.06 (169.05) |
| +XH-14C (3 μM) | 0.171 (1.80) | 0.216\*\*\* (2.27) |
| +MK571 (5 μM) | 0.164 (1.73) | 0.232\*\*\* (2.27) |
| Cisplatin | 1.793 (1.00) | 2.233 (1.25) |
| +XH-14C (3 μM) | 1.698 (0.95) | 1.845 (1.03) |
| +MK571 (5 μM) | 1.496 (0.83) | 1.725 0.96) |

[1]RF, resistance fold, calculated by dividing the IC$_{50}$ value in the drug-induced ABCC1-overexpressing cancer cell line KB-CV60 by the IC$_{50}$ value in the parental cancer cell line KB-3-1.
\*\*\*means p < 0.001, compared with the value of KB-CV60 control group.

TABLE 6

Reversal effects of peptides on transfected ABCC1-overexpressing cell lines

| Treatment | IC$_{50}$ (μM) (RF[1]) | |
|---|---|---|
| | HEK293/pcDNA3.1 | HEK293/ABCC1 |
| Vincristine | 0.137 (1.00) | 2.710 (19.79) |
| +XH-14C (3 μM) | 0.138 (1.01) | 0.142\*\*\* (1.04) |
| +MK571 (5 μM) | 0.140 (1.02) | 0.138\*\*\* (1.01) |
| Cisplatin | 2.214 (1.00) | 2.235 (1.01) |
| +XH-14C (3 μM) | 2.157 (0.97) | 2.271 (1.03) |
| +MK571 (5 μM) | 2.201 (0.99) | 2.456 (1.11) |

[1]R, resistance fold, calculated by dividing the IC$_{50}$ value in the transfected ABCC1-overexpressing cell line HEK293/ABCC1 by the IC$_{50}$ value in the transfected empty vector cell line HEK293/pcDNA3.1.
\*\*\*means p < 0.001, compared with the value of HEK293/ABCC1 control group.

EXAMPLE 5

Effect of Peptide XH-14C on the Expression of ABCB1 Transporter

Figure 1B:
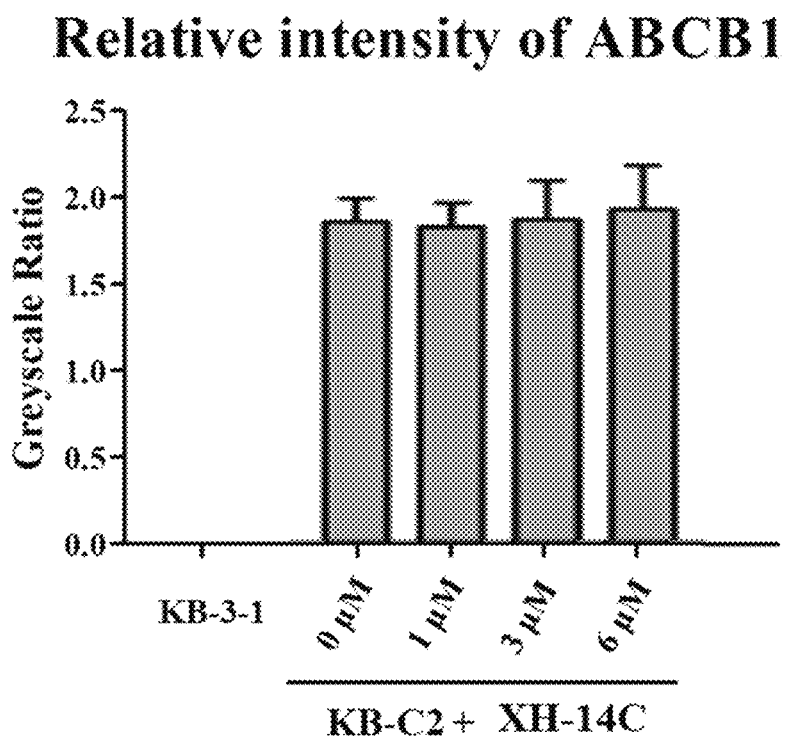
FIG. 1B illustrates relative intensity of the expression of ABCB1 to the expression of GAPDH.

Western blotting analysis was performed to investigate whether the peptide XH-14C affects the expression of ABCB1 transporter. KB-C2 and untreated KB-3-1 cells were treated with 0 μM, 1 μM, 3 μM and 6 μM of the peptide XH-14C for 72 h, and then incubated with lysis buffer (containing 2.5% 1M Tris, 0.15% EDTA, 1% sodium deoxycholate, 0.1% SDS, 0.88% NaCl, 1% Triton-X and a protease inhibitor) on ice for 20 min, and centrifuged at 4° C. to collect a supernatant. The protein concentration of the supernatant was determined by the bicinchoninic acid (BCA)-based protein assay. Each protein sample was loaded and separated by SDS-polyacrylamide gel electrophoresis. After that, the gel was transferred to a polyvinylidene fluoride (PVDF) membrane. After blocked with 5% milk for 2 h, the PVDF membrane was incubated with primary antibodies (1:1000 dilution for both anti-P-glycoprotein and anti-GAPDH antibodies) at 4° C. overnight. Then the PVDF membrane was washed with TBST buffer (Tris buffer, 0.1% Tween 20), and incubated with a secondary HRP-labeled antibody (1:1000 dilution for an anti-mouse antibody). The signal was detected by enhanced chemiluminescence method, and the protein expression was quantified by software. As shown in FIGS. 1A and 1B, The treatment of different concentrations (0 μM, 1 μM, 3 μM and 6 μM) of the peptide XH-14C did not significantly affect the expression of ABCB1 protein (172 kDa) in the KB-C2 cells.

EXAMPLE 6

Effect of Peptide XH-14C on the Expression of ABCC1 Transporter

Figure 2A:
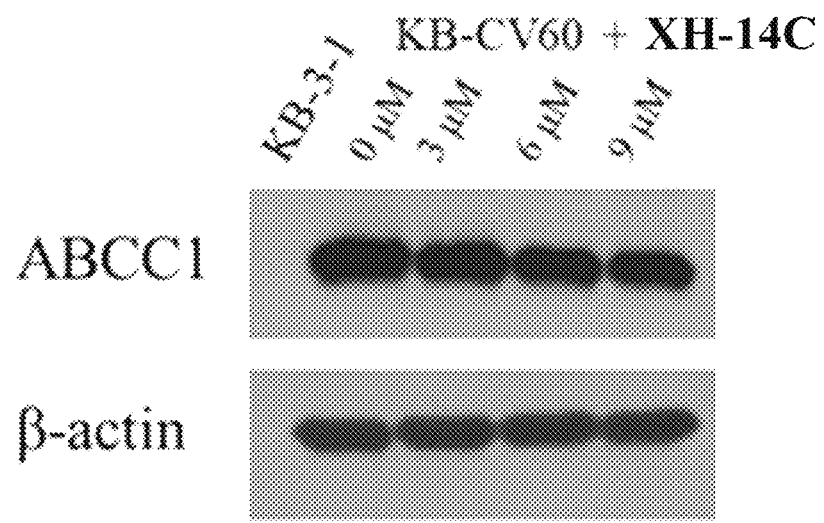
FIG. 2A shows expression of ABCC1 protein in KB-CV60 cells after incubation with different concentrations of peptide XH-14C for 72 h; where KB-3-1 cells without any treatment are used as a negative control, and GAPDH is used as loading control.
Figure 2B:
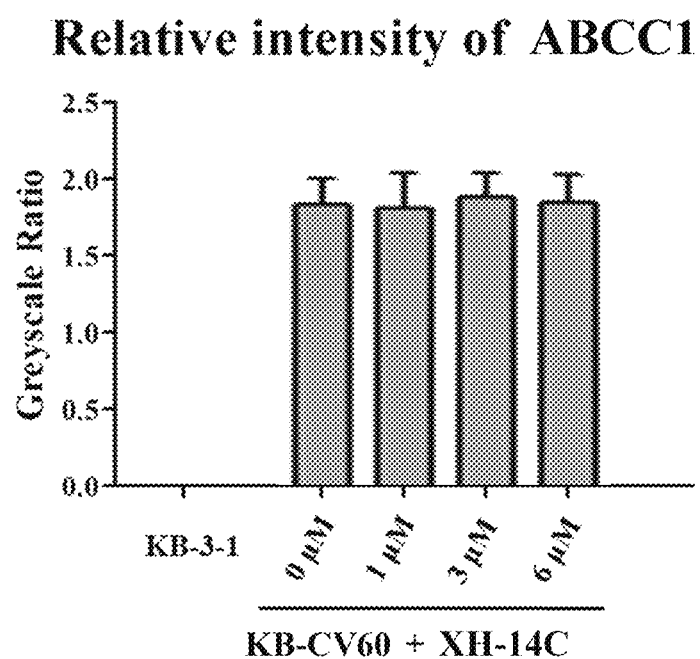
FIG. 2B illustrates relative intensity the expression of of ABCC1 to the expression of GAPDH.

Western blotting analysis was performed to investigate whether the peptide XH-14C affects the expression of ABCC1 transporter. KB-CV60 and untreated KB-3-1 cells were treated with 0 µM, 1 µM, 3 µM and 6 µM of the peptide XH-14C for 72 h, and then incubated with lysis buffer (containing 2.5% 1M Tris, 0.15% EDTA, 1% sodium deoxy cholate, 0.1% SDS, 0.88% NaC1, 1% Triton-X and a protease inhibitor) on ice for 20 min, and centrifuged at 4° C. to collect a supernatant. The protein concentration of the supernatant was determined by the bicinchoninic acid (BCA)-based protein assay. Each protein sample was loaded and separated by SDS-polyacrylamide gel electrophoresis. After that, the gel was transferred to a polyvinylidene fluoride (PVDF) membrane. After blocked with 5% milk for 2 h, the PVDF membrane was incubated with primary antibodies (1:1000 dilution for both anti-P-glycoprotein and anti-GAPDH antibodies) at 4° C. overnight. Then the PVDF membrane was washed with TBST buffer (Tris buffer, 0.1% Tween 20), and incubated with a secondary HRP-labeled antibody (1:1000 dilution for an anti-mouse antibody). The signal was detected by enhanced chemiluminescence method, and the protein expression was quantified by software. As shown in FIGS. 2A and 2B, The treatment of different concentrations (0 µM, 1 µM, 3 µM and 6 µM) of the peptide XH-14C did not significantly affect the expression of ABCC1 protein (190 kDa) in the KB-CV60 cells.

EXAMPLE 7

Effect of Peptide XH-14C on Expression Level and Cell Localization of ABCB1

Figure 3:
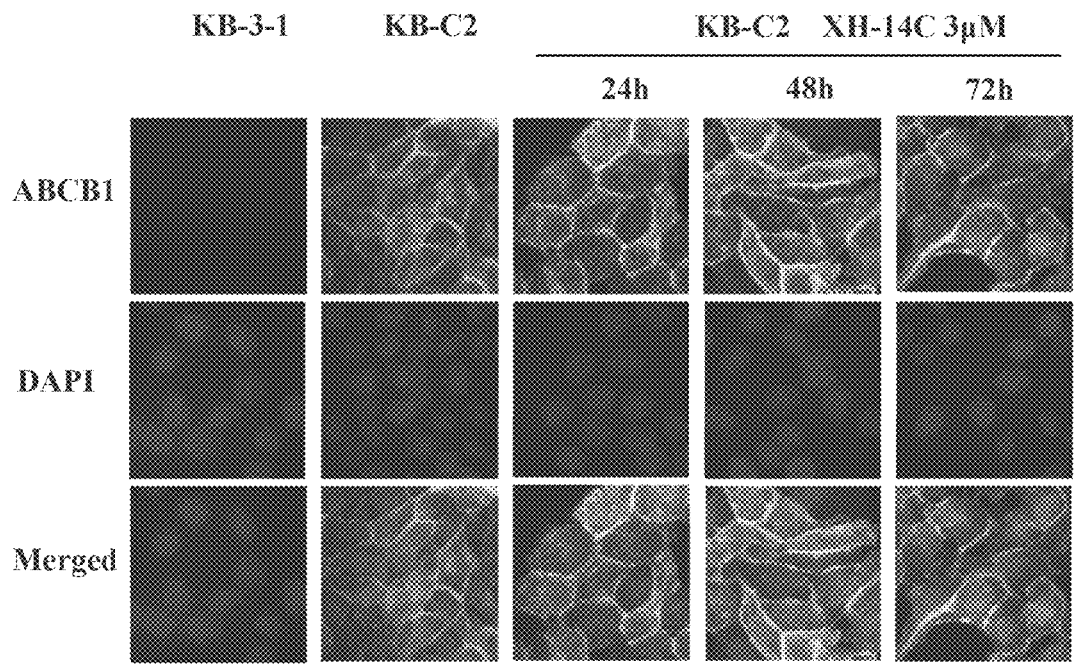
FIG. 3 shows an effect of the peptide XH-14C on the expression of ABCB1 in KB-3-1 and KB-C2 cells and subcellular localization.

In order to further confirm whether the peptide affected the expression level and cell localization of the ABCB1 protein, immunofluorescent staining was performed on the cells after different incubation times of the peptide XH-14C. The KB-3-1 and KB-C2 cells were seeded in 24-well plates ($1 \times 10^4$ cells/well), and incubated at 37° C. for 24 h, and then incubated with 3 µM of the peptide XH-14C for 0 h, 24 h, 48 h and 72 h, respectively. The cells were washed twice with cold PBS solution, fixed in 4% formaldehyde for 15 min, and then permeabilized with 0.25% Triton X-100 for 15 min. After incubated with BSA (6% in PBS) for 1 h, the cells were incubated with monoclonal anti-Pglycoprotein Clone F4 primary antibody with a dilution of 1:1000 at 4° C. overnight, and then further incubated with Alexa Fluor 488 conjugated rabbit anti-mouse IgG secondary antibody with dilution of 1:1000 for 1 h in the dark. The nuclei were counterstained with DAPI solution and observed with a fluorescence microscope. As shown in FIG. 3, compared to the parental cells KB-3-1, ABCB1 was significantly expressed on the cell membrane of KB-C2. The fluorescence intensity of ABCB1 in KB-C2 remained unchanged after treated with the peptide XH-14C, which was consistent with the results of Western blotting analysis. In addition, the peptide XH-14C had no significant effect on the subcellular distribution pattern of ABCB1 on the KB-C2 cell membrane. These results indicated that the reversal of MDR by the peptide XH-14C was not caused by the decrease of protein expression or the change of protein location.

EXAMPLE 8

Effect of Peptide XH-14C on Expression Level and Cell Localization of ABCC1

Figure 4:
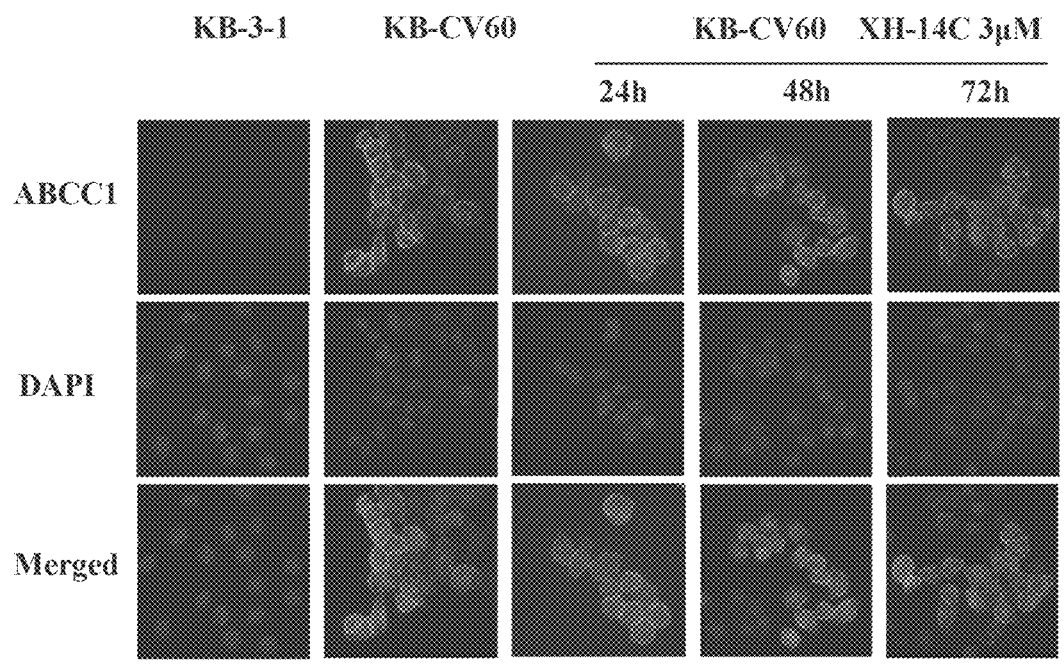
FIG. 4 shows an effect of the peptide XH-14C on the expression of ABCC1 in KB-3-1 and KB-CV60 cells and subcellular localization.

In order to further confirm whether the peptide affected the expression level and cell localization of the ABCC1 protein, immunofluorescent staining was performed on the cells after different incubation times of the peptide XH-14C. The KB-3-1 and KB-CV60 cells were seeded in 24-well plates ($1 \times 10^4$ cells/well), and incubated at 37° C. for 24 h, and then incubated with 3 µM of the peptide XH-14C for 0 h, 24 h, 48 h and 72 h, respectively. The cells were washed twice with cold PBS solution, fixed in 4% formaldehyde for 15 min, and then permeabilized with 0.25% Triton X-100 for 15 min. After incubated with BSA (6% in PBS) for 1 h, the cells were incubated with monoclonal anti-Pglycoprotein Clone F4 primary antibody with a dilution of 1:1000 at 4° C. overnight, and then further incubated with Alexa Fluor 488 conjugated rabbit anti-mouse IgG secondary antibody with dilution of 1:1000 for 1 h in the dark. The nuclei were counterstained with DAPI solution and observed with a fluorescence microscope. As shown in FIG. 4, compared to the parental cells KB-3-1, ABCC1 was significantly expressed on the cell membrane of KB-CV60. The fluorescence intensity of ABCC1 in KB-CV60 remained unchanged after treated with the peptide XH-14C, which was consistent with the results of Western blotting analysis. In addition, the peptide XH-14C had no significant effect on the subcellular distribution pattern of ABCC1 on the KB-CV60 cell membrane. These results indicated that the reversal of MDR by the peptide XH-14C was not caused by the decrease of protein expression or the change of protein location.

EXAMPLE 9

Effect of Peptide XH-14C on Accumulation and Efflux of [$^3$H]-Paclitaxel

Figure 5:
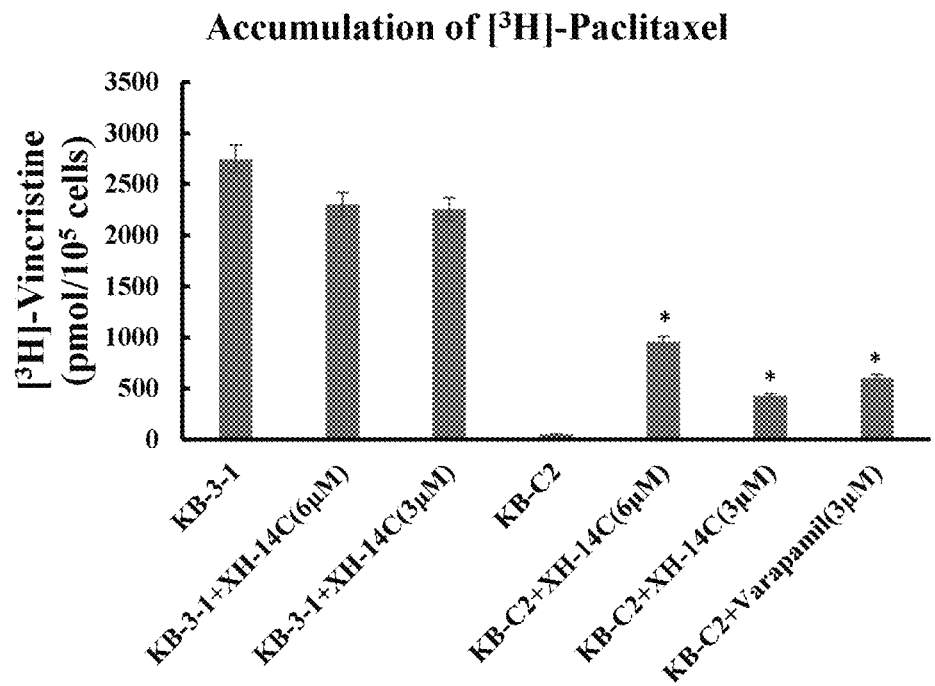
FIG. 5 shows an effect of the peptide XH-14C on accumulation of [$^3$H]-paclitaxel in KB-3-1 and KB-C2 cells.
Figure 6:
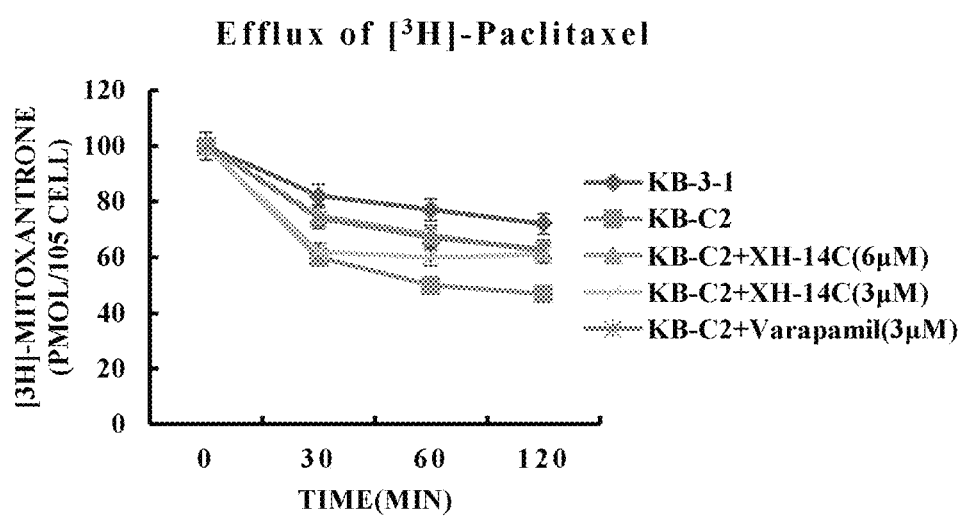
FIG. 6 shows an effect of the peptide XH-14C on efflux of [$^3$H]-paclitaxel in KB-3-1 and KB-C2 cells.

The effect of the peptide XH-14C on the accumulation and efflux of [$^3$H]-paclitaxel in ABCB1-overexpressing cells was determined by comparing the concentration of [$^3$H]-paclitaxel in KB-3-1 and KB-C2 cells. The KB-3-1 and KB-C2 cells were seeded in a 24-well plate ($1 \times 10^4$ cells/well), incubated at 37° C. for 24 h, and then incubated in the presence or absence of the peptide XH-14C and the positive reversal agent verapamil for 72 h. After that, the medium was replaced with a medium containing 5 µM [$^3$H]-paclitaxel and peptide XH-14C or the positive reversal agent. The drug-containing medium was discarded after 2 h incubation. The cells were washed three times with a cold PBS buffer and transferred to a scintillation fluid. The efflux analysis was performed in a way similar to the accumulation analysis. After discarding the medium containing [$^3$H]-paclitaxel, the cells were washed with cold PBS, and incubated with a medium containing the peptide XH-14C or a positive reversal agent. Three sampling time points (30 min, 60 min and 120 min) were set, at which the cells were collected, washed three times, and then transferred to the scintillation fluid. The radioactivity was measured with a liquid scintillation analyzer. The results were shown in FIG. 5. The level of [$^3$H]-paclitaxel in ABCB1-overexpressing KB-C2 cells was approximately 100 times that of the parental KB-3-1 cells after 2 h of the incubation. Compared with the control group, the accumulation of [$^3$H]-paclitaxel in the KB-C2 cells incubated with the peptide XH-14C (3 µM) was significantly enhanced, and the effect of the peptide XH-14C (3 μM) on the accumulation of [$^3$H]-paclitaxel was similar to that of the ABCB1 inhibitor verapamil (3 μM). In addition, the effect of the peptide XH-14C on the efflux of [$^3$H]-paclitaxel in ABCB1-overexpressing KB-C2 cells was also evaluated herein, and the results were shown in FIG. 6. After incubated with the peptide XH-14C for 2 h, the [$^3$H]-paclitaxel level in KB-3-1 cells did not change significantly, and the inhibitor verapamil did not change the efflux function of KB-3-1 cells. However, the [$^3$H]-paclitaxel level in the KB-C2 cells without inhibitor treatment significantly decreased by about 50%, which indicated that the peptide XH-14C (3 μM) can effectively inhibit the efflux function of KB-C2 cells.

EXAMPLE 10

Effect of Peptide XH-14C on Accumulation and Efflux of [$^3$H]-Vincristine

Figure 7A:
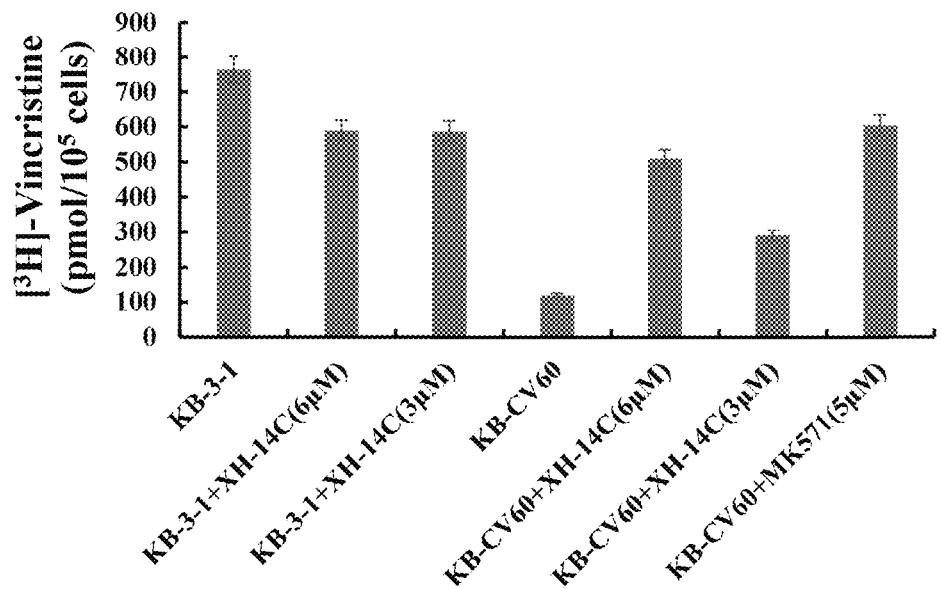
FIG. 7A shows an effect of the peptide XH-14C on accumulation of [$^3$H]-vincristine in KB-3-1 and KB-CV60 cells.
Figure 7B:
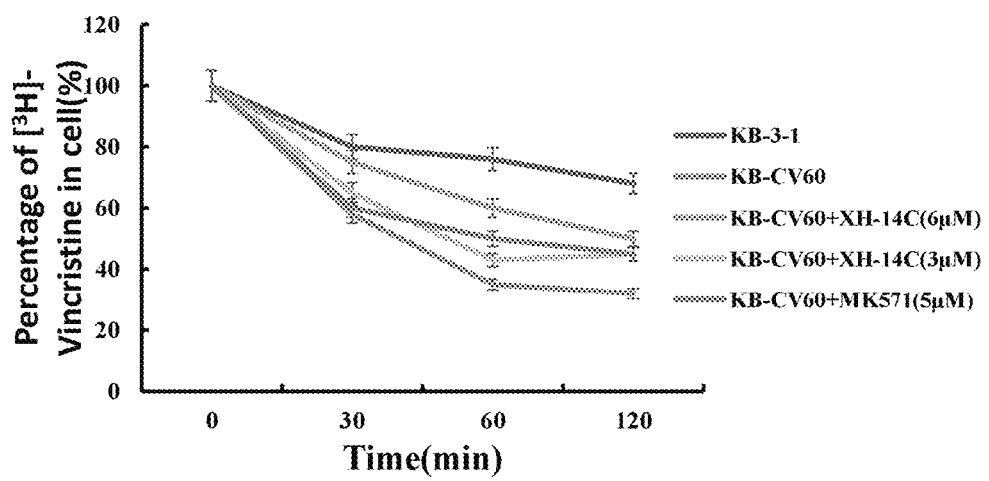
FIG. 7B depicts an effect of the peptide XH-14C on efflux of vincristine in KB-3-1 and KB-CV60 cells.

The effect of the peptide XH-14C on the accumulation and efflux of [$^3$H]-vincristine in ABCC1-overexpressing cells was determined by comparing the concentration of [$^3$H]-vincristine in KB-3-1 and KB-CV60 cells. The KB-3-1 and KB-CV60 cells were seeded in a 24-well plate ($1\times10^4$ cells/well), incubated at 37° C. for 24 h, and then incubated in the presence or absence of the peptide XH-14C and the positive reversal agent MK571 for 72 h. After that, the medium was replaced with a medium containing 5 μM [$^3$H]-vincristine and peptide XH-14C or the positive reversal agent. The drug-containing medium was discarded after 2 h incubation. The cells were washed three times with a cold PBS buffer transferred to a scintillation fluid. The efflux analysis was performed in a way similar to the accumulation analysis. After discarding the medium containing [$^3$H]-vincristine, the cells were washed with cold PBS, and incubated with a medium containing the peptide XH-14C or a positive reversal agent. Three sampling time points (30 min, 60 min and 120 min) were set, at which the cells were collected, washed three times, and then transferred to the scintillation fluid. The radioactivity was measured with a liquid scintillation analyzer. The results were shown in FIG. 7A. The level of [$^3$H]-vincristine in ABCC1-overexpressing KB-CV60 cells was approximately 7 times that of the parental KB-3-1 cells after 2 h of the incubation. Compared with the control group, the accumulation of [$^3$H]-vincristine in the KB-CV60 cells incubated with the peptide XH-14C (3 μM) was significantly enhanced. In addition, the effect of the peptide XH-14C on the efflux of [$^3$H]-vincristine in ABCC1-overexpressing KB-CV60 cells was also evaluated herein, and the results were shown in FIG. 7B. After incubated with the peptide XH-14C for 2 h, the [$^3$H]-vincristine level in KB-3-1 cells was decreased by 25%. However, the [$^3$H]-vincristine level in the KB-CV60 cells without inhibitor treatment significantly decreased by about 70%, [$^3$H]-vincristine in KB-CV60 cells treated with peptide XH-14C (3 μM) decreased by 55%, which was equivalent to the effect of inhibitor MK571. The results indicated that the peptide XH-14C (3 μM) can effectively inhibit the efflux function of KB-CV60 cells.

EXAMPLE 11

Effect of Peptide XH-14C on ATPase Activity of ABCB1 Transporter

Figure 8:
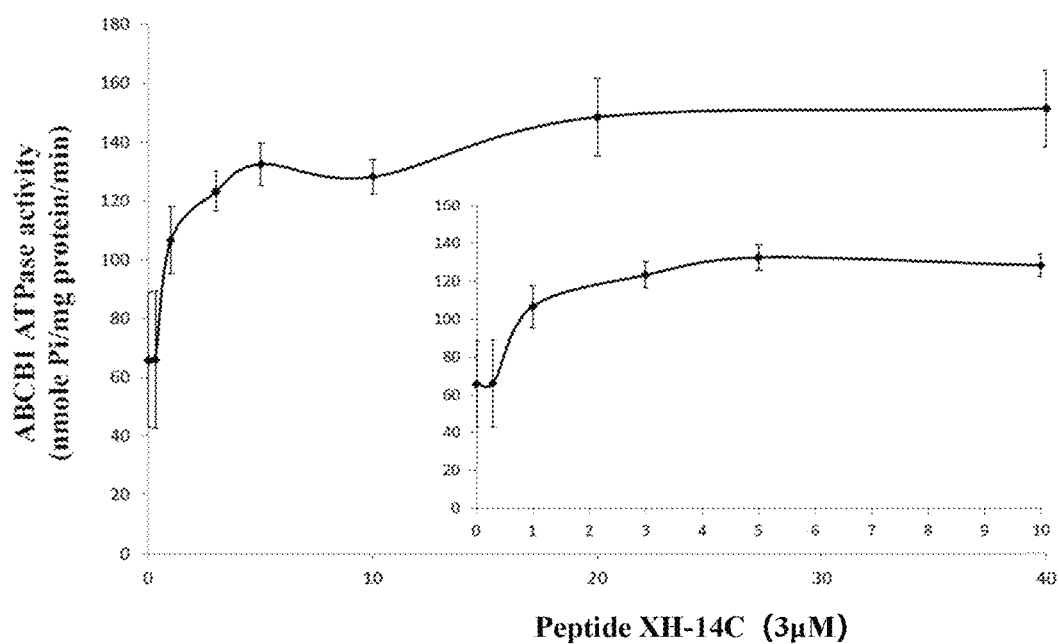
FIG. 8 shows an effect of the peptide XH-14C on ATPase activity of ABCB1.

The hydrolysis of ATP mediated by ABCB1 in the presence of different concentrations (0-40 μM) of the peptide XH-14C was investigated to evaluate the effect of the peptide XH-14C on the ATPase activity of ABCB1. The membrane vesicles (10 μg protein) were incubated in ATPase buffer at 37° C. with or without 0.3 mM vanadate for 5 min. The peptide XH-14C at a concentration of 0-40 μM was added to the ATPase buffer and the cells were incubated at 37° C. for 3 min, to which 0.1 mL of 5 mM Mg-ATP was added to initiate the ATPase reaction. After incubating at 37° C. for 20 min, 100 μL of 5% SDS solution was added to stop the reaction. The ATPase activity was calculated according to the released inorganic phosphorus (IP) measured at 800 nm with a spectrophotometer. The results were shown in FIG. 8. The peptide XH-14C stimulated the ATPase activity of ABCB1 in a concentration-dependent manner, and the maximum stimulation amount was 2.3 times the basic activity. The concentration of the peptide XH-14C required for 50% stimulation of the ATPase activity was 0.65 μM, which was much lower than the cytotoxic concentration. These results indicated that the peptide XH-14C may interact with the drug substrate binding site, thereby affecting the ATPase activity of ABCB1.

EXAMPLE 12

Molecular Docking Analysis of Peptide XH-14C-ABCB1

Figure 9A:
FIGS. 9A-9C show a molecular docking of peptide XH-14C and ABCB1; where 9A: domains and positions of ABCB1 binding with the peptide XH-14C; 9B: a surface structure of peptide XH-14C-ABCB1 complex; and 9C: predicted binding mode of the peptide XH-14C with ABCB1.
Figure 9B:
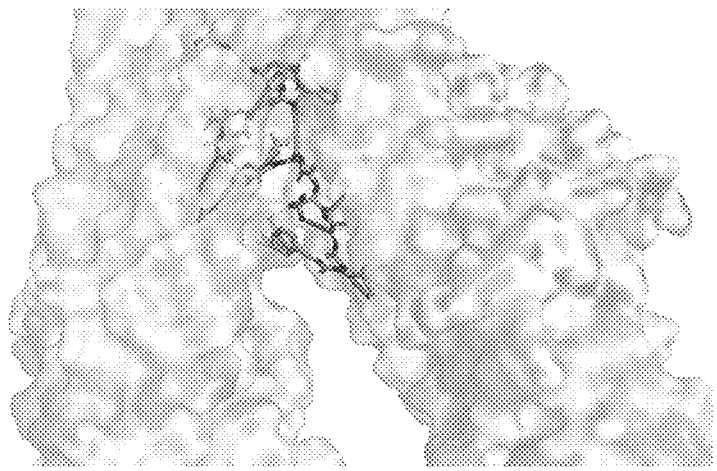
Figure 9C:
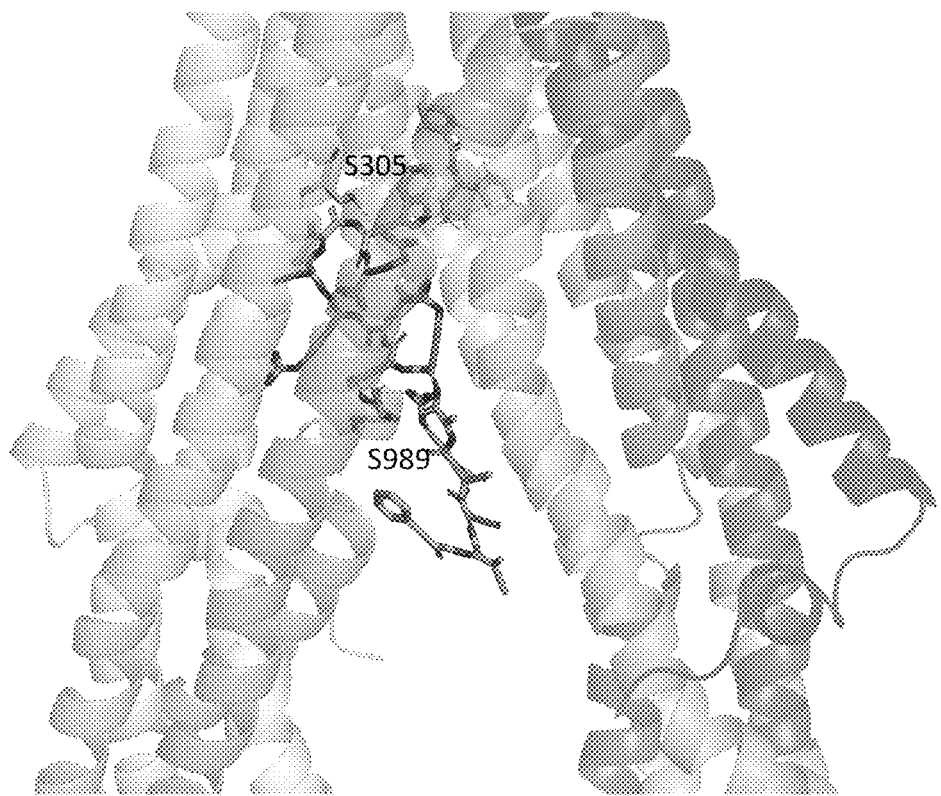

In order to further investigate the potential binding mode and rationalize the observation effect of the peptide XH-14C, a molecular docking study was performed. The peptide XH-14C was depicted by Sybyl/Sketch module (Tripos Inc.), optimized by applying Powell's method with Tripos force field with convergence criterion set at 0.05 kcal/(Åmol), and assigned by the Gasteiger-Hsckel method. The crystal structure of ABCB1 was obtained from the RCSB protein database (PDB-ID: 4M2T). Using ligand-based mode, peptide XH-14C was docked into the active sites of ABCB1. The ligand was removed, and hydrogen was added and minimized using Tripos force field and Pullman charges. Other docking parameters remained default values. The results were shown in FIGS. 9A-9C, the peptide XH-14C was tightly bound to the active site (substrate binding site) of ABCB1. The hydrogen bonds were formed between the peptide and the S305 and S989 residues in ABCB1, which may play an important role in improving the binding affinity of the peptide XH-14C and ABCB1.

EXAMPLE 13

Molecular Docking Analysis of Peptide XH-14C-ABCC1

Figure 10A:
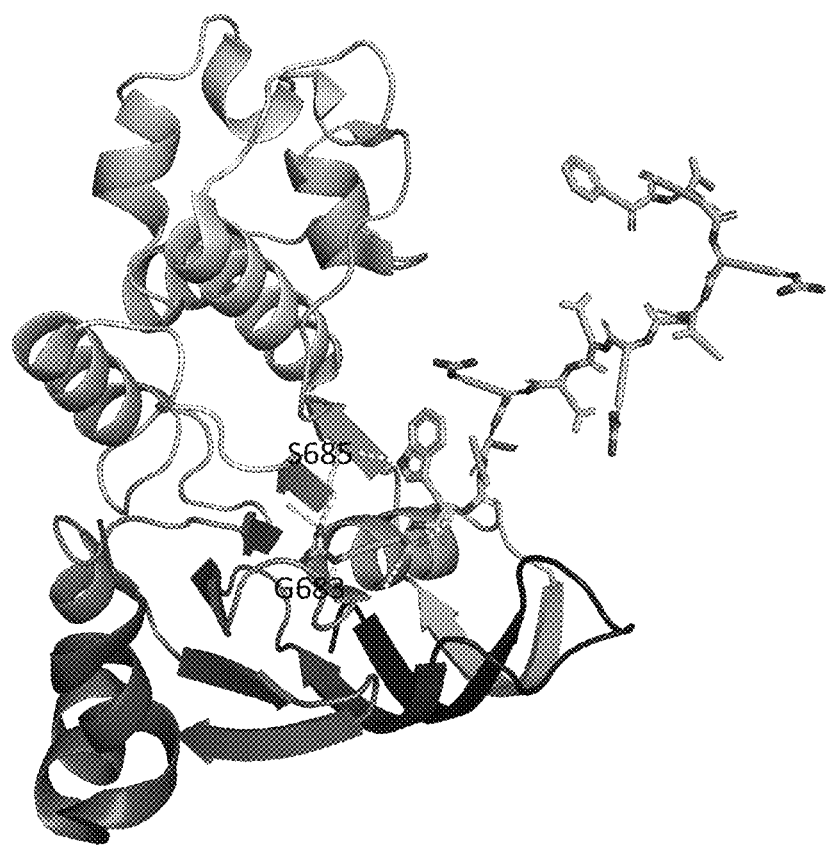
FIGS. 10A-10B show a molecular docking of peptide XH-14C and ABCC1; where 10A: domains and positions of ABCC1 binding with the peptide XH-14C; and 10B: a surface structure of peptide XH-14C-ABCC1 complex.
Figure 10B:
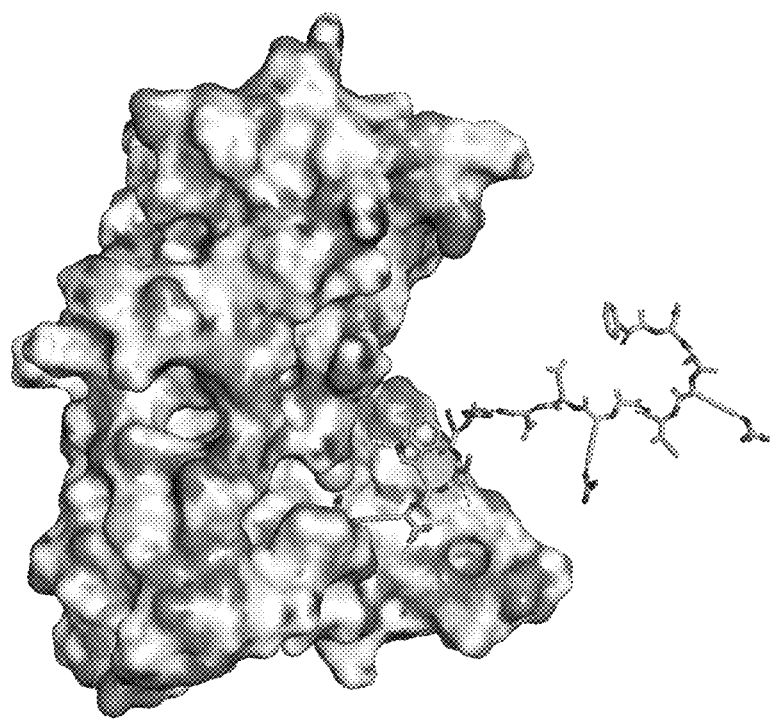

In order to further investigate the potential binding mode and rationalize the observation effect of the peptide XH-14C, a molecular docking study was performed. The peptide XH-14C was depicted by Sybyl/Sketch module (Tripos Inc.), optimized by applying Powell's method with Tripos force field with convergence criterion set at 0.05 kcal/(Åmol), and assigned by the Gasteiger-Hsckel method. The crystal structure of ABCC1 was obtained from the RCSB protein database (PDB-ID: 4M2T). Using ligand-based mode, peptide XH-14C was docked into the active sites of ABCC1. The ligand was removed, and hydrogen was added and minimized using Tripos force field and Pullman charges. Other docking parameters remained default values. The results were shown in FIGS. 10A-10B, from which it can be seen that the peptide XH-14C was tightly bonded to the nucleotide binding domain (NBD) of ABCC1. The hydrogen bonds were formed between the peptide and the S685 and G683 residues in ABCC1.

What is claimed is:

1. A method for treating a tumor with multidrug resistance mediated by an ABC transporter in a subject in need thereof, comprising:
   administering a peptide XH-14C shown in SEQ ID NO: 1 to the subject;
   wherein the ABC transporter is ABCB1 or ABCC1.

2. A method for treating a tumor with multidrug resistance mediated by an ABC transporter in a subject in need thereof, comprising:
   administering a composition of a peptide XH-14C shown in SEQ ID NO: 1 and an ABC transporter substrate chemotherapeutic drug to the subject.

3. The method of claim 2, wherein the ABC transporter is ABCB1 or ABCC1.

4. The method of claim 3, wherein when the ABC transporter is ABCB1, the tumor is lung cancer, cervical cancer, human epidermoid carcinoma, ovarian cancer, liver cancer, intestinal cancer, gastric cancer or pancreatic cancer; and when the ABC transporter is ABCC1, the tumor is lung cancer, liver cancer, intestinal cancer, breast cancer or esophageal cancer.

5. The method of claim 4, wherein when the ABC transporter is ABCB1, the ABC transporter substrate chemotherapeutic drug is selected from the group consisting of taxanes, vinca alkaloids, anthracyclines, epipodophyllotoxins, tyrosine kinase inhibitors and antitumor antibiotics; and when the ABC transporter is ABCC1, the ABC transporter substrate chemotherapeutic drug is selected from the group consisting of vinca alkaloids, anthracyclines, epipodophyllotoxins and tyrosine kinase inhibitors.

6. The method of claim 5, wherein when the ABC transporter is ABCB1, the ABC transporter substrate chemotherapeutic drug is selected from the group consisting of paclitaxel, docetaxel, vinblastine, vincristine, doxorubicin, daunorubicin, etoposide, teniposide, imatinib, nilotinib, erlotinib, actinomycin D and a combination thereof; and when the transporter is ABCC1, the ABC transporter substrate chemotherapeutic drug is selected from the group consisting of anthracycline, vinca alkaloid, epipodophyllotoxin, camptothecin, methotrexate, saquinavir, mitoxantrone, imatinib and a combination thereof.

7. A pharmaceutical composition for treating a tumor with multidrug resistance mediated by an ABC transporter, comprising:
   a peptide XH-14C shown in SEQ ID NO: 1 and an ABC transporter substrate chemotherapeutic drug.

8. The pharmaceutical composition of claim 7, wherein the ABC transporter is ABCB1 or ABCC1.

9. The pharmaceutical composition of claim 8, wherein when the ABC transporter is ABCB1, the ABC transporter substrate chemotherapeutic drug is selected from the group consisting of taxanes, vinca alkaloids, anthracyclines, epipodophyllotoxins, tyrosine kinase inhibitors and antitumor antibiotics; when the ABC transporter is ABCC1, the ABC transporter substrate chemotherapeutic drug is selected from the group consisting of vinca alkaloids, anthracyclines, epipodophyllotoxins and tyrosine kinase inhibitors.

* * * * *